(12) United States Patent
Uchida

(10) Patent No.: US 9,693,685 B2
(45) Date of Patent: Jul. 4, 2017

(54) IMAGING APPARATUS, CONTROL METHOD OF THE SAME, AND PROGRAM

(75) Inventor: Koji Uchida, Utsunomiya (JP)

(73) Assignee: Canon Kabushiki Kaisha, Tokyo (JP)

( * ) Notice: Subject to any disclaimer, the term of this patent is extended or adjusted under 35 U.S.C. 154(b) by 514 days.

(21) Appl. No.: 13/699,597

(22) PCT Filed: May 18, 2011

(86) PCT No.: PCT/JP2011/002774
§ 371 (c)(1),
(2), (4) Date: Nov. 21, 2012

(87) PCT Pub. No.: WO2011/148597
PCT Pub. Date: Dec. 1, 2011

(65) Prior Publication Data
US 2013/0077047 A1    Mar. 28, 2013

(30) Foreign Application Priority Data

May 26, 2010 (JP) .................................. 2010-120801

(51) Int. Cl.
| | | |
|---|---|---|
| A61B 3/14 | (2006.01) | |
| A61B 3/00 | (2006.01) | |
| A61B 3/12 | (2006.01) | |
| G03B 17/48 | (2006.01) | |
| H04N 5/33 | (2006.01) | |

(52) U.S. Cl.
CPC .................. *A61B 3/12* (2013.01); *A61B 3/14* (2013.01); *G03B 17/48* (2013.01); *H04N 5/33* (2013.01)

(58) Field of Classification Search
USPC .................................................. 351/206, 246
See application file for complete search history.

(56) References Cited

U.S. PATENT DOCUMENTS

| | | | |
|---|---|---|---|
| 5,897,229 | A | 4/1999 | Kawakami |
| 2004/0070672 | A1 | 4/2004 | Iwami |
| 2008/0055419 | A1 | 3/2008 | Ito |

FOREIGN PATENT DOCUMENTS

| | | |
|---|---|---|
| CN | 1487724 A | 4/2004 |
| JP | 59-186540 A | 10/1984 |
| JP | 11-119326 A | 4/1999 |
| JP | 2000-232961 A | 8/2000 |
| JP | 2002-028134 A | 1/2002 |
| JP | 2003-216374 A | 7/2003 |
| JP | 2006-042922 A | 2/2006 |
| JP | 2006-158822 A | 6/2006 |
| JP | 2008-119201 A | 5/2008 |
| WO | 2009/050339 A1 | 4/2009 |

*Primary Examiner* — Jack Dinh
(74) *Attorney, Agent, or Firm* — Canon USA, Inc. I.P. Division

(57) ABSTRACT

An imaging apparatus includes an image sensor sensitive to infrared rays, and a control circuit. The control circuit determines whether the imaging apparatus is mounted on a fundus camera in a state where an image of a fundus of a subject's eye can be captured based on reflected light flux from the fundus, and controls a function of the imaging apparatus depending on the determination.

10 Claims, 4 Drawing Sheets

IMAGING APPARATUS, CONTROL METHOD OF THE SAME, AND PROGRAM

TECHNICAL FIELD

The present invention relates to a technology to capture images of a fundus of a subject's eye.

BACKGROUND ART

Conventional fundus cameras each have a single-lens reflex digital camera as its photographing unit. When a photographing switch on a joy stick of the fundus camera is pressed, the digital camera of the imaging unit captures an image of a target. In capturing an image, photographing conditions (e.g., ISO sensitivity and shutter speed) may be directly set using user interface switches of the digital camera (hereinafter, referred to as user interface (UI) switches), or set through an external personal computer (PC) in communication with the digital camera.

Japanese Patent Application Laid-Open No. 2003-216374 discusses a technology of printer driver that makes inaccessible commands available to users in its maintenance mode. Japanese Patent Application Laid-Open No. 11-119326 discusses a technology to provide a function to accept a password to a single-lens reflex digital camera such that an input of a password can cancel a state of the camera that prohibits photographing. In such digital cameras as imaging units of conventional fundus cameras, however, the UI switches are arranged on a face thereof. As a result, operation errors in pressing switches to change photographing conditions may occur, and operators may forget to restore settings for a new subject and thereby capture images in inappropriate photographing conditions. In other cases, another error may happen: even when photographing conditions are already set using an external PC, an operator, without knowing it, may change the photographing conditions using UI switches, and a next operator does not notice the change and capture images under the conditions as they are.

Digital cameras sensitive to infrared rays are sometimes used as photographing units of fundus cameras. These digital cameras can be detached from the photographing units of fundus cameras to capture images with a lens for a general-use single-lens reflex camera. The digital cameras are, however, sensitive to infrared rays, and may capture images operator does not intend or expect.

CITATION LIST

Patent Literature

PTL 1: Japanese Patent Application Laid-Open No. 2003-216374

PTL 2: Japanese Patent Application Laid-Open No. 11-119326

SUMMARY OF INVENTION

The present invention is directed to provide an imaging apparatus that offers an appropriate use depending on the state the imaging apparatus is set.

According to an aspect of the present invention, an imaging apparatus of the present invention can be removably mounted on a fundus camera, and includes: an imaging unit sensitive to infrared rays; a determination unit configured to determine whether the imaging apparatus is mounted on a fundus camera in a state where an image of a fundus of a subject's eye can be captured based on reflected light flux from the fundus; and a control unit configured to control a function of the imaging apparatus depending on the determination made by the determination unit.

The present invention enables an appropriate use of an imaging apparatus depending on the state the imaging apparatus is set.

Further features and aspects of the present invention will become apparent from the following detailed description of exemplary embodiments with reference to the attached drawings.

BRIEF DESCRIPTION OF DRAWINGS

The accompanying drawings, which are incorporated in and constitute a part of the specification, illustrate exemplary embodiments, features, and aspects of the invention and, together with the description, serve to explain the principles of the invention.

DESCRIPTION OF EMBODIMENTS

Various exemplary embodiments, features, and aspects of the invention will be described in detail below with reference to the drawings.

Figure 1:
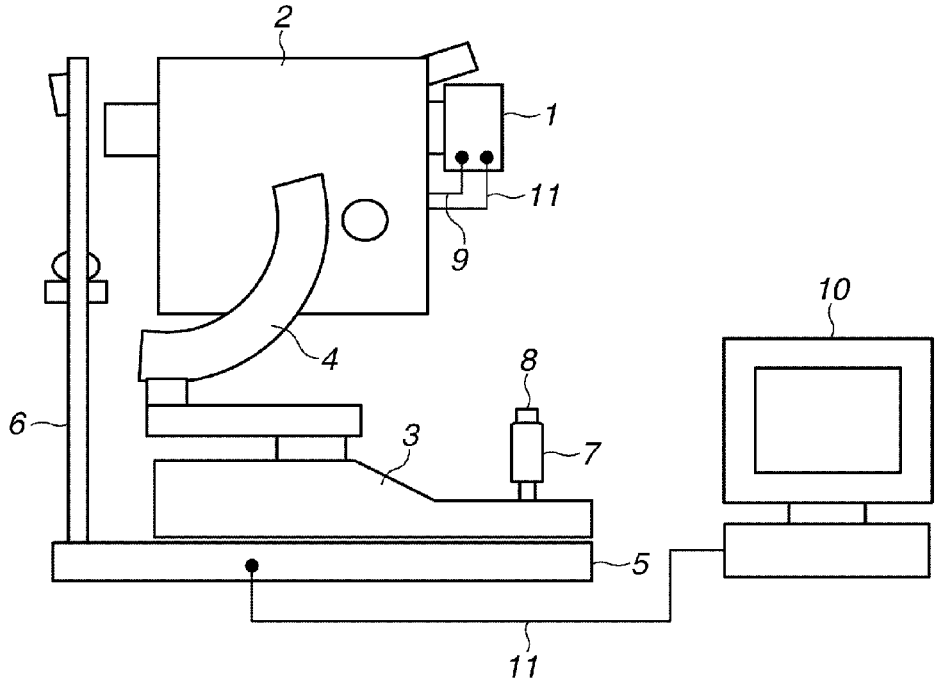
FIG. 1 illustrates a structure of a fundus camera system of an exemplary embodiment according to the present invention.

FIG. 1 illustrates a structure of a fundus camera system of an exemplary embodiment according to the present invention. In FIG. 1, a digital camera 1 is connected to a photographing optical system 2 of the fundus camera. The photographing optical system 2 is arranged in a movable manner relative to a subject's eye in the direction of elevation angle using a frame 4 supported by a rack 3. The photographing optical system 2 is configured to input light flux that is reflected from a fundus of the subject's eye into the digital camera 1 when the digital camera 1 is connected thereto. A base 5 supports a face support unit 6 that fixes a subject's face. The rack 3 having the photographing optical system 2 is movable in the front, back, right, and left directions relative to the face support unit 6 as operated by an operation lever 7. The operation lever 7 has a photographing switch 8. When the photographing switch 8 is pressed, a release signal to start photographing is transmitted through a cable 9 to the digital camera 1. The digital camera 1 is also connected to an external PC 10 via the fundus camera and a communication cable 11. Image data photographed by the digital camera 1 is transferred to the external PC 10 via the communication cable 11. The photographing conditions used in the digital camera 1 can be set by transmitting the photographing conditions set in the external PC 10 to the digital camera 1.

Figure 2:
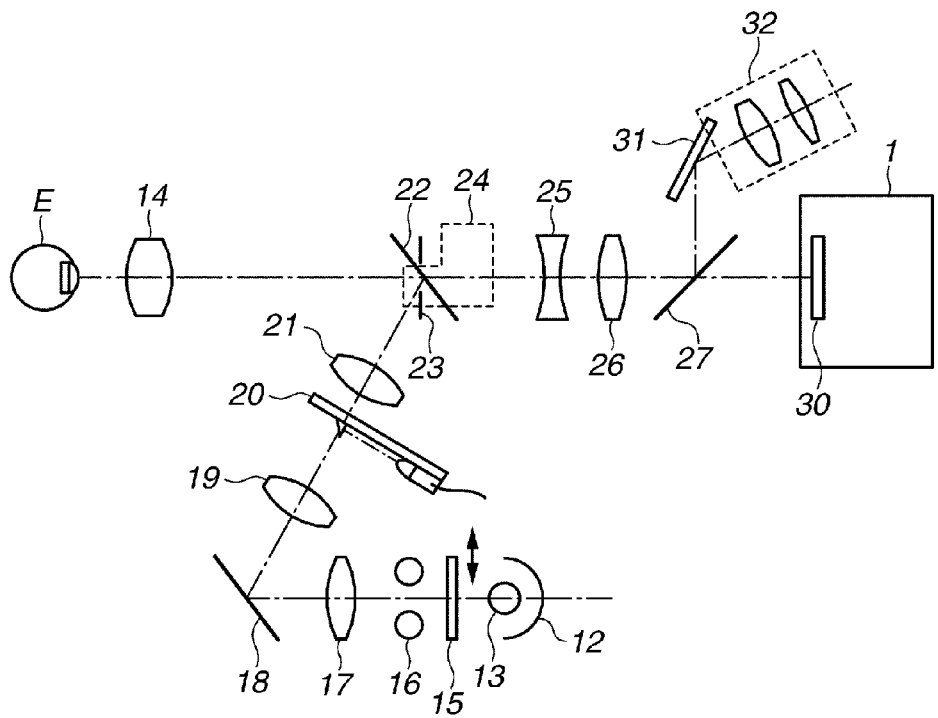
FIG. 2 illustrates an inner structure of the photographing optical system of the fundus camera in FIG. 1.

FIG. 2 illustrates a structure of the photographing optical system 2 of a fundus camera. An illumination optical system is provided between a halogen lamp 13 at the center of a reflective hemispherical mirror 12 and an objective lens 14. In observation of a fundus, a light flux emitted from the halogen lamp 13 passes a removable visible-light cut filter 15, a stroboscopic tube 16 as light source for photographing, and a lens 17, and is reflected at a folding mirror 18. The reflected light flux passes a first relay lens 19, a split projection unit 20 for focus adjustment, and a second relay lens 21, and is reflected at an aperture mirror 22. The reflected light flux enters the objective lens 14 to be projected on the pupil of the subject's eye in a circular shape to illuminate a fundus plane.

The light flux is then reflected on the fundus plane, and passes the center of the ring on the pupil, the objective lens 14, and the aperture mirror 22. A diaphragm 23 is disposed near the reflective plane of the aperture mirror 22. Downstream of the diaphragm 23, an operation distance index projection system 24, a focusing lens 25, an imaging lens 26, a quick-return mirror 27 partially reflecting visible light, and the digital camera 1 are arranged in sequence. The digital camera 1 includes an imaging plane 30 that is disposed to correspond to a conjugate plane of a fundus. In the reflected direction from the quick-return mirror 27, a mirror 31 and a finder lens group 32 are arranged.

For visible light observation of a fundus E, the fundus camera retracts the visible-light cut filter 15 from the optical path, so that an operator can observe the fundus E through the finder lens group 32. For infrared light observation of the fundus E, the fundus camera inserts the visible-light cut filter 15 into the optical path and flips up the quick-return mirror 27, so that an image of the fundus is captured on the imaging plane 30. The digital camera 1 sensitive to infrared rays can provide images of a fundus for observation. In the image capturing, the stroboscopic tube 16 emits light, which passes the same optical path to be received at the imaging plane 30. In this way, image data of a fundus is captured.

Figure 3:
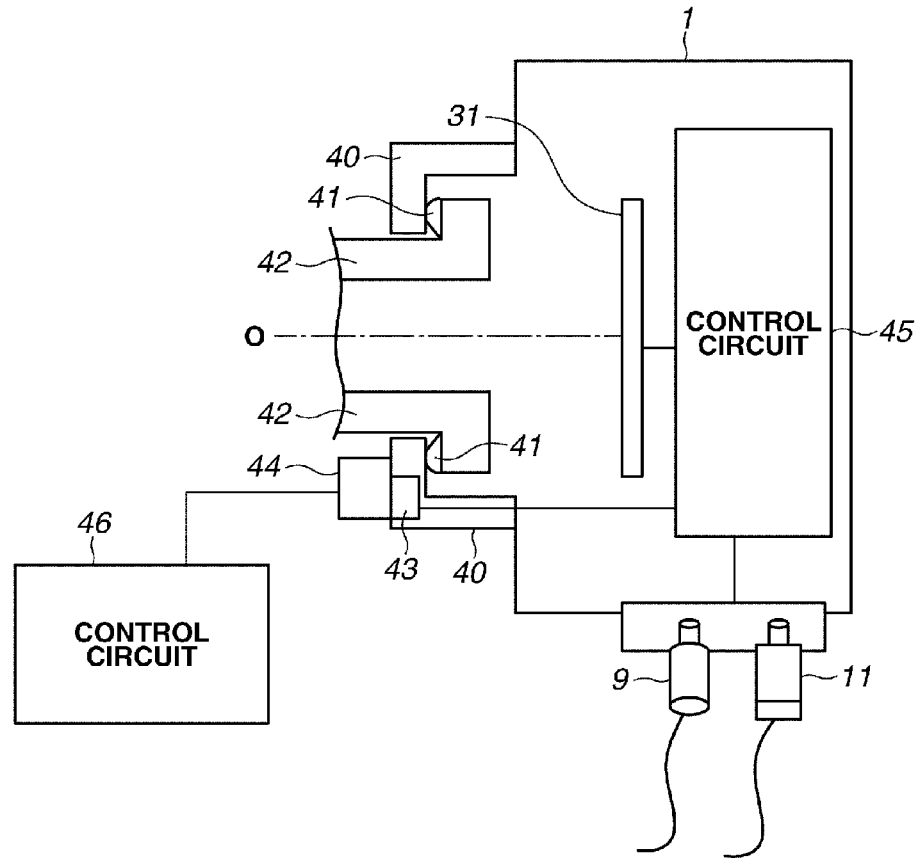
FIG. 3 illustrates junction between a photographing optical system of a fundus camera and a digital camera.

FIG. 3 illustrates junction between the photographing optical system 2 of a fundus camera and a digital camera 1. The photographing optical system 2 has an optical axis O for photographing, and the digital camera 1 has an image sensor 31 (imaging plane 30) located at a position conjugated with the fundus plane. The digital camera 1 has a mount unit 40 rotatable around the optical axis O, and a leaf spring 41 is incorporated therein such that the mount unit 40 can be rotatable relative to and removable from a fixed mount 42 placed on the photographing optical system 2. When assembled in the correct orientation, a junction terminal 43 (also referred to as a first member) of the mount unit 40 and a junction terminal 44 (also referred to as a second member) of the fixed mount 42 are coupled to each other and electrically connected. The junction terminal 43 is connected to a control circuit 45 of the digital camera 1. The junction terminal 44 is connected to a control circuit 46 in the photographing optical system 2.

Figure 4:
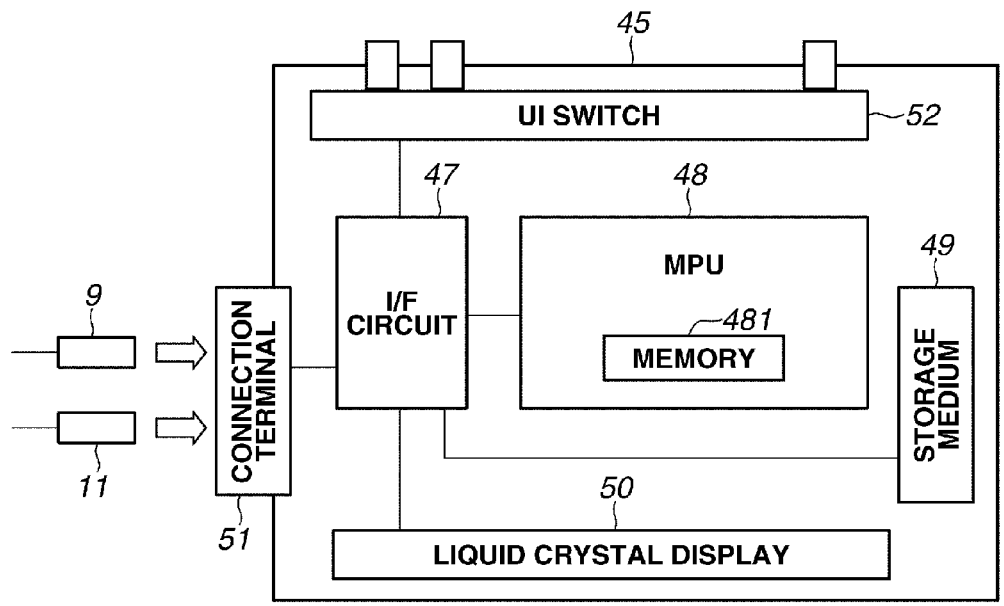
FIG. 4 illustrates a structure of a control circuit of a digital camera.

FIG. 4 illustrates a structure of the control circuit of 45 a digital camera 1. The image sensor 31 outputs image data, which is received by a micro-processing unit (MPU) 48 via an interface circuit 47. The digital camera 1 has UI switches 52 including a photographing switch, an ISO sensitivity change switch, a shutter speed change switch which are all arranged on a face of the digital camera 1. The UI switches 52 are connected to the MPU 48 via the interface circuit 47. The MPU 48 has firmware incorporated therein to control image capturing processing, image processing, processing of communication with external devices, and controlling of the UI switches. The MPU 48 further has a memory 481 incorporated therein, the memory 481 storing predetermined image data. The interface circuit 47 is connected to a storage medium 49 storing captured image data. The interface circuit 47 is also connected to a liquid crystal display 50 displaying the captured image data. The control circuit 45 is provided with a connection terminal 51 to transmit and receive communication signals from the fundus camera and communication signals from the external PC 10. A communication cable 9 transmits a release signal from the photographing switch 8 of the fundus camera to the digital camera 1. The communication cable 11 transmits captured image data to the external PC 10, and receives photographing conditions and patient information from the external PC 10. In FIG. 4, the junction terminal 43 is connected to an interface circuit 47 (not illustrated). Accordingly, the digital camera 1 can determine whether the junction terminal 43 of the digital camera 1 is connected to the junction terminal 44 of the fundus camera.

Figure 5:
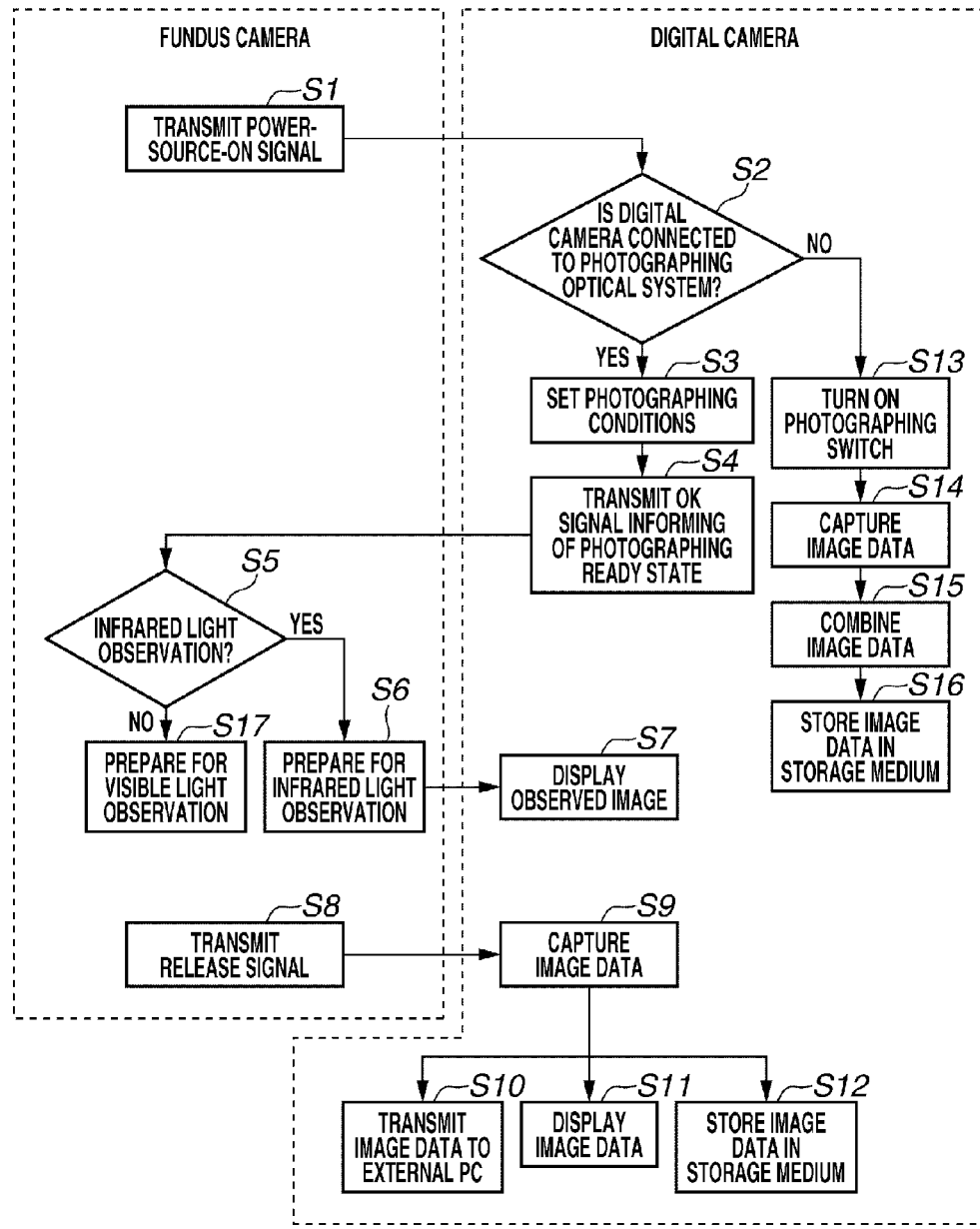
FIG. 5 is a flowchart illustrating operations in a fundus camera and a digital camera.

FIG. 5 is a flowchart illustrating operations processed in the fundus camera and the digital camera 1. With reference to FIG. 5, the case where the junction terminal 43 at the mount 40 of the digital camera 1 is connected to the junction terminal 44 at the fixed mount 42 of the fundus camera, and a case where the junction terminal 43 is not connected to the junction terminal 44 are described.

In step S1, when an operator turns on the fundus camera, the control circuit 46 of the fundus camera transmits a power-source ON signal to the digital camera 1, and thereby power is also supplied to the digital camera 1. In step S2, the MPU 48 of the digital camera 1 determines whether digital camera 1 is connected to the photographing optical system 2 in a state enabling the digital camera 1 to capture images of a fundus. When the digital camera 1 is connected to the photographing optical system 2 (YES in step S2), the process proceeds to step S3.

In step S3, the MPU 48 sets predetermined photographing conditions. The setting in step S3 includes an input of a patient information ID from the external PC 10, and change in photographing conditions made at the external PC 10. The MPU 48, then, prohibits operations of the digital camera 1 operable through the operation members arranged on a face thereof such as the photographing switch, the ISO sensitivity change switch, and the shutter speed change switch. The prohibition prevents error operation of the digital camera 1 when the digital camera 1 is connected to the photographing optical system 2 and used for observation. After setting the photographing conditions of the digital camera 1, in step S4, the MPU 48 transmits an OK signal notifying a state ready for photographing, to the control circuit 46 of the photographing optical system 2 via communication through mounts.

When receiving the OK signal indicating a photographing ready state, the control circuit 46 of the photographing optical system 2 determines whether a fundus observation is to be performed with visible light (visible light observation) or a fundus observation is to be performed with infrared light (infrared light observation), according to the setting made by the operator. In step S5, in the case of infrared light observation, the control circuit 46 inserts the visible-light cut filter 15 to the optical path, and flips up the quick-return mirror 27. In step S6, when the photographing optical system 2 gets ready for an infrared light observation, the control circuit 46 transmits a signal informing that the photographing optical system 2 is ready for image capture by infrared light, to the digital camera 1. In step S7, the MPU 48 displays image data observed using the infrared light on the liquid crystal display 50. In contrast, in the case of visible light observation, in step S17, the control circuit 46 retracts the visible-light cut filter 15 from the optical path to prepare the photographing optical system 2 for a visible light observation. In step S8, when the operator aligns the photographing optical system 2 with a subject's eye, and presses the photographing switch 8 of the operation lever 7, the control circuit 46 of the fundus camera transmits a release signal to the digital camera 1.

In step S9, when receiving the release signal from the fundus camera, the MPU 48 loads the image data on the memory 481. The loaded image data is transmitted to the external PC 10 in step S10, displayed on the liquid crystal display 50 in step S11, or stored in the storage medium 49 in step S12, depending on the initial setting of the digital camera.

Figure 6:
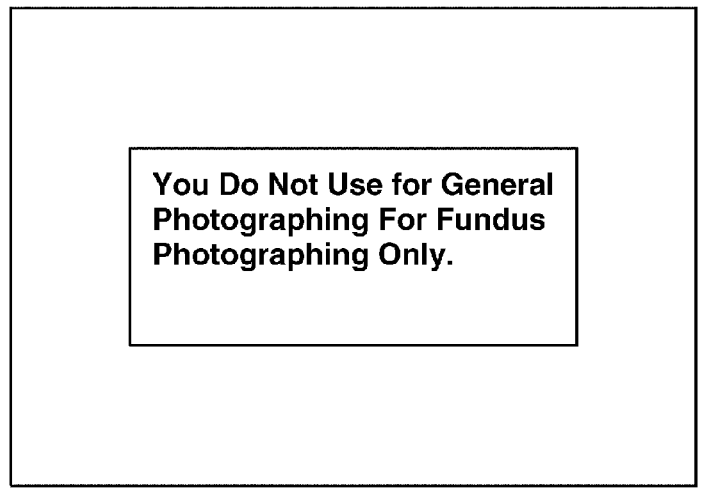
FIG. 6 illustrates data of a message image to inform or alert user.
Figure 7:
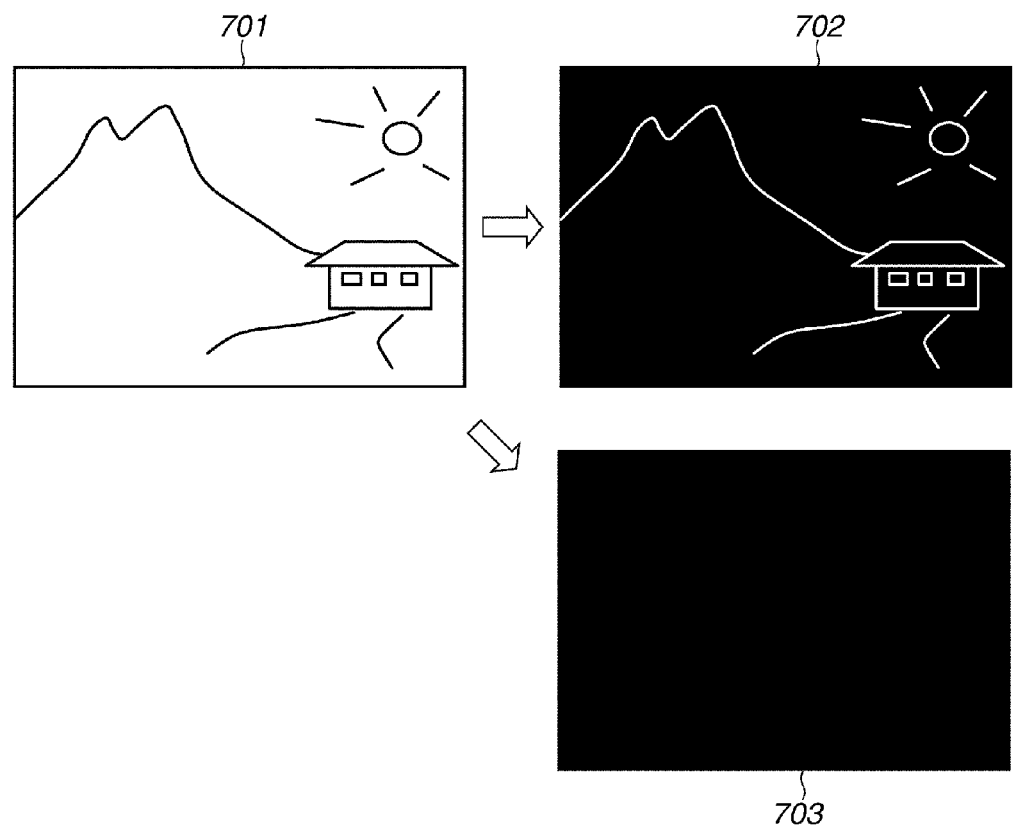
FIG. 7 illustrates a captured image data with color determined, and an image data generally having darker tint.

If, in step 2, it is determined the digital camera 1 is not connected to the photographing optical system 2, the process proceeds to step S13. In the present invention, the digital camera 1 is manufactured only for image capturing of fundus and is sensitive to infrared light. Accordingly, it is obvious that the digital camera 1 cannot be used with a lens for general cameras. If an operator removes the digital camera 1 from the photographing optical system 2 and uses it as a general-purpose camera, unexpected and undesirable situation happens to the operator. Thus, in the present exemplary embodiment, when an operator removes the digital camera 1 from the photographing optical system 2 and uses it, the following process is executed. In step S13, when the photographing switch of the digital camera 1 is turned on, in step S14, the MPU 48 loads image data on the memory 481. In step S15, the MPU 48 combines predetermined image data with the loaded image data. In step S16, the MPU 48 outputs the combined image data generated in step S15 to the storage medium 49 as captured image data, and stores it there. Examples of the combined image data includes, as illustrated in FIG. 6, data of a message image superimposed on the loaded image data for informing or alerting the operator. Instead of step S15, as illustrated in FIG. 7, image data 702 in reversed color of the captured image data (the loaded image data) 701 may be generated, or image data 703 in darker tint may be generated. Such image generation can prevent inappropriate leakage of image data from the digital camera 1. After the digital camera 1 is again mounted on the photographing optical system 2, the image processing on the image data as shown in step S15 is canceled. In addition, the prohibition of the image processing on the image data as shown in step S15, the recording of the captured image and the like, is also referred to as a state disabling predetermined photographing by the imaging apparatus.

In the above exemplary embodiment, whether the connection is established between the photographing optical system 2 and the digital camera 1 is determined based on the communication available at the mount unit. In another exemplary embodiment, whether the connection is established may be determined based on the connection of the communication cable 9 of the photographing switch 8 or the communication cable 11 extending from the external PC 10 with the connection terminal 51 of the digital camera, which provides the same effect as in the above exemplary embodiment.

The present invention can also be achieved by executing the following processing. Software (program) executing the functions of the above exemplary embodiments is supplied to a system or apparatus via a network or various storage media, and a computer in the system or apparatus (or control processing unit (CPU) or MPU) reads and executes the program.

OTHER EMBODIMENTS

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (e.g., computer-readable medium).

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

This application claims priority from Japanese Patent Application No. 2010-120801 filed May 26, 2010, which is hereby incorporated by reference herein in its entirety.

The invention claimed is:

1. An imaging apparatus that can be removably mounted on an ophthalmologic apparatus, the ophthalmologic apparatus comprising an illumination optical system configured to irradiate a subject's eye with light emitted from a light source through an objective lens, the imaging apparatus comprising:
   an imaging unit sensitive to infrared light; and
   a control unit configured to control a function of the imaging apparatus so as to prohibit operations to be performed through an operation switch of the imaging apparatus when the imaging apparatus is mounted on the ophthalmologic apparatus in a state where an image of a fundus of the subject's eye can be captured with infrared light and so as to perform operations through the operation switch when the imaging apparatus is not mounted on the ophthalmologic apparatus in the state.

2. The imaging apparatus according to claim 1, wherein the control unit controls the imaging apparatus so that a state disabling predetermined photographing is canceled when the imaging apparatus is mounted on the ophthalmologic apparatus in a state where the image of the fundus can be captured with infrared light.

3. The imaging apparatus according to claim 2, wherein a determination unit determines whether the imaging apparatus is mounted on the ophthalmologic apparatus in a state enabling capture of images of the fundus, based on a connection state between an imaging optical system for inputting light flex from the fundus to the imaging apparatus and the imaging apparatus.

4. The imaging apparatus according to claim 1, further comprising a display unit configured to display the image of the fundus with infrared light.

5. The imaging apparatus according to claim 1, wherein the operation switch is a photographing switch, an ISO sensitivity change switch, or a shutter speed change switch.

6. A method of controlling an imaging apparatus that can be removably mounted on an ophthalmologic apparatus and has an imaging unit sensitive to infrared light, the ophthalmologic apparatus comprising an illumination optical system configured to irradiate a subject's eye with light emitted from a light source through an objective lens, the method comprising:

determining whether the imaging apparatus is mounted on an ophthalmologic apparatus in a state where an image of a fundus of the subject's eye can be captured with infrared light; and controlling a function of the imaging apparatus so as to prohibit operations to be performed through an operation switch of the imaging apparatus when the imaging apparatus is mounted on the ophthalmologic apparatus in the state and so as to perform operations through the operation switch when the imaging apparatus is not mounted on the ophthalmologic apparatus in the state.

7. A program that causes a computer to execute a method of controlling an imaging apparatus that can be removably mounted on an ophthalmologic apparatus and has an imaging unit sensitive to infrared light, the ophthalmologic apparatus comprising an illumination optical system configured to irradiate a subject's eye with light emitted from a light source through an objective lens, the method comprising:

determining whether the imaging apparatus is mounted on an ophthalmologic apparatus in a state where an image of a fundus of the subject's eye can be captured with infrared light; and controlling a function of the imaging apparatus so as to prohibit operations to be performed through an operation switch of the imaging apparatus when the imaging apparatus is mounted on the ophthalmologic apparatus in the state and so as to perform operations through the operation switch when the imaging apparatus is not mounted on the ophthalmologic apparatus in the state.

8. An ophthalmic system, comprising:

an ophthalmologic apparatus that comprises an illumination optical system configured to irradiate a subject's eye with light emitted from a light source through an objective lens;

an imaging apparatus that can be removably mounted on the ophthalmologic apparatus and has an imaging unit sensitive to infrared light; and a control apparatus that controls the imaging apparatus so as to prohibit operations to be performed through an operation switch of the imaging apparatus when the imaging apparatus is mounted on the ophthalmologic apparatus in a state where an image of a fundus of a subject's eye can be captured with infrared light and so as to perform operations through the operation switch when the imaging apparatus is not mounted on the ophthalmologic apparatus in the state.

9. The ophthalmic system according to claim 8, wherein the imaging apparatus includes a first member, wherein the ophthalmologic apparatus includes a second member, wherein the control apparatus includes a determination unit configured to determine that the imaging apparatus is mounted on the ophthalmologic apparatus in a state enabling capture of an image of the fundus when the first and second members are disposed at predetermined positions respectively.

10. The ophthalmic system according to claim 9, wherein the first member and the second member are respectively a junction terminal, and wherein the determination unit determines that the imaging apparatus is mounted on the ophthalmologic apparatus in a state enabling capture of an image of the fundus when the first member and the second member are connected.

* * * * *